United States Patent
Kantro

(10) Patent No.: US 7,337,680 B2
(45) Date of Patent: Mar. 4, 2008

(54) SYSTEM AND METHOD FOR MEASURING PLANTAR FOOT PRESSURE

(76) Inventor: Scott Kantro, 23 Split Rock Rd., Pound Ridge, NY (US) 10576

( * ) Notice: Subject to any disclaimer, the term of this patent is extended or adjusted under 35 U.S.C. 154(b) by 157 days.

(21) Appl. No.: 10/538,560

(22) PCT Filed: Dec. 10, 2003

(86) PCT No.: PCT/US03/39321

§ 371 (c)(1), (2), (4) Date: Feb. 27, 2006

(87) PCT Pub. No.: WO2004/055483

PCT Pub. Date: Jul. 1, 2004

(65) Prior Publication Data

US 2007/0137295 A1    Jun. 21, 2007

Related U.S. Application Data

(60) Provisional application No. 60/433,282, filed on Dec. 13, 2002.

(51) Int. Cl.
G01L 1/26    (2006.01)
G01L 5/04    (2006.01)

(52) U.S. Cl. ............................................... 73/862.391
(58) Field of Classification Search ............ 73/862.391
See application file for complete search history.

(56) References Cited

U.S. PATENT DOCUMENTS

| | | | | |
|---|---|---|---|---|
| 4,858,621 A | | 8/1989 | Franks | 128/779 |
| 5,195,030 A | * | 3/1993 | White | 705/26 |
| 5,678,566 A | * | 10/1997 | Dribbon | 600/592 |
| 5,790,256 A | * | 8/1998 | Brown et al. | 356/613 |
| 5,885,223 A | | 3/1999 | Yamato et al. | 600/592 |
| 6,122,846 A | * | 9/2000 | Gray et al. | 36/136 |
| 6,205,230 B1 | | 3/2001 | Sundman et al. | 382/100 |
| 6,216,545 B1 | * | 4/2001 | Taylor | 73/862.046 |
| 6,331,893 B1 | * | 12/2001 | Brown et al. | 356/601 |
| 6,752,028 B2 | * | 6/2004 | Bechmann | 73/862.391 |
| 2005/0171456 A1 | * | 8/2005 | Hirschman et al. | 600/592 |

OTHER PUBLICATIONS

PCT Search report Dec. 10, 2003.

* cited by examiner

Primary Examiner—Edward Lefkowitz
Assistant Examiner—Octavia Davis
(74) Attorney, Agent, or Firm—Sofer & Haroun, LLP

(57) ABSTRACT

A measuring device (10) is used for generating an imprint of a patient's foot. The imprint includes a first set of at least two differentiable color density markings. The first set of differentiable density markings each correspond to a different pressure exerted on the measuring device by different areas of the patient's foot. A calibration card (50) is provided with an indicia including a set of at least two differentiable density markings. Each differentiable density marking in the second set of differentiable density markings on the calibration card has a viewing opening (56) disposed within, such that when the viewing openings in the calibration card are placed over the imprint of the patient's foot, the first set of different density markings from the imprint are viewable through the viewing openings so that they are readably comparable to the second set of differentiable density markings in the indicia on the calibration card.

10 Claims, 7 Drawing Sheets

SYSTEM AND METHOD FOR MEASURING PLANTAR FOOT PRESSURE

RELATED APPLICATIONS

This application is a 371 of PCT/US03/39321.

This application is related to and claims the benefit of priority from U.S. Provisional Patent Application No. 60/433,282, filed on Dec. 13, 2002, the entirety of which is incorporated herein by reference.

FIELD OF THE INVENTION

The present invention is related to a system and method for measuring plantar foot pressure. More specifically, the present invention is directed to a system and method for low-cost, accurate plantar foot pressure measurement.

BACKGROUND OF THE INVENTION

It is well known that plantar ulcerations, commonly found in diabetic persons, develop in the feet over areas of high pressure. In these situations, the ulcerations can be associated with motor neuropathy, foot deformation, limited joint mobility, callus formation, even foot amputation. It is also known that high-pressure areas have been clinically proven as indicators of the likelihood of development of these plantar foot ulcers in neuropathic feet. In fact, it has been shown that among patients presenting with neuropathy, those with a reading of $\geq 6$ kg/cm$^2$ were twice as likely to develop a foot ulcer.

Reducing the pressure in the high-pressure areas of the foot of the affected person may prevent or reduce the effects of plantar ulcerations. Thus, early detection of high-pressure areas is essential in preventing the onset of plantar foot ulcerations, particularly in those patients considered at high risk.

Many methods have been developed in the past to measure plantar foot pressure, however, these methods are often costly and require special training to operate the necessary devices. Therefore, there exists a need to provide a low-cost, efficient and reliable means for measuring plantar foot pressure, particularly in high risk patients such as diabetics, so as to detect high-pressure areas in order to prevent plantar foot ulcerations.

SUMMARY OF THE INVENTION

The present invention overcomes the drawbacks associated with the prior art foot pressure measuring systems and provides for a low-cost, efficient and reliable means for measuring plantar foot pressure for detecting "high-pressure" areas in order to prevent plantar foot ulcerations.

To this end, the present invention provides for a plantar foot pressure measuring device, having a layer of pressure sensitive ink. A cover sheet is activated by removing its backing layer and the pressure sensitive ink is transferred to the cover sheet when the patient places a foot onto the pressure measuring device forming a gray-scaled plantar pressure foot print. The ink layer is removed and the cover, with pressure foot print thereon, is placed onto a grid sheet to permanently fix the print between the cover sheet and a grid sheet on the pressure measuring device.

A calibration card is provided having a corresponding gray-scale that is used to compare with areas on the pressure foot print. Using the gray-scale on the calibration card the user is able to determine the plantar foot pressure that was measured by the pressure measuring device, within a given set of pressure ranges.

DETAILED DESCRIPTION

The present invention maintains a pressure measuring device 10 for measuring the plantar foot pressure of a patient. A calibration card 50 is used in conjunction with pressure measuring device 10 in order to discern the measured pressures.

Figure 1:
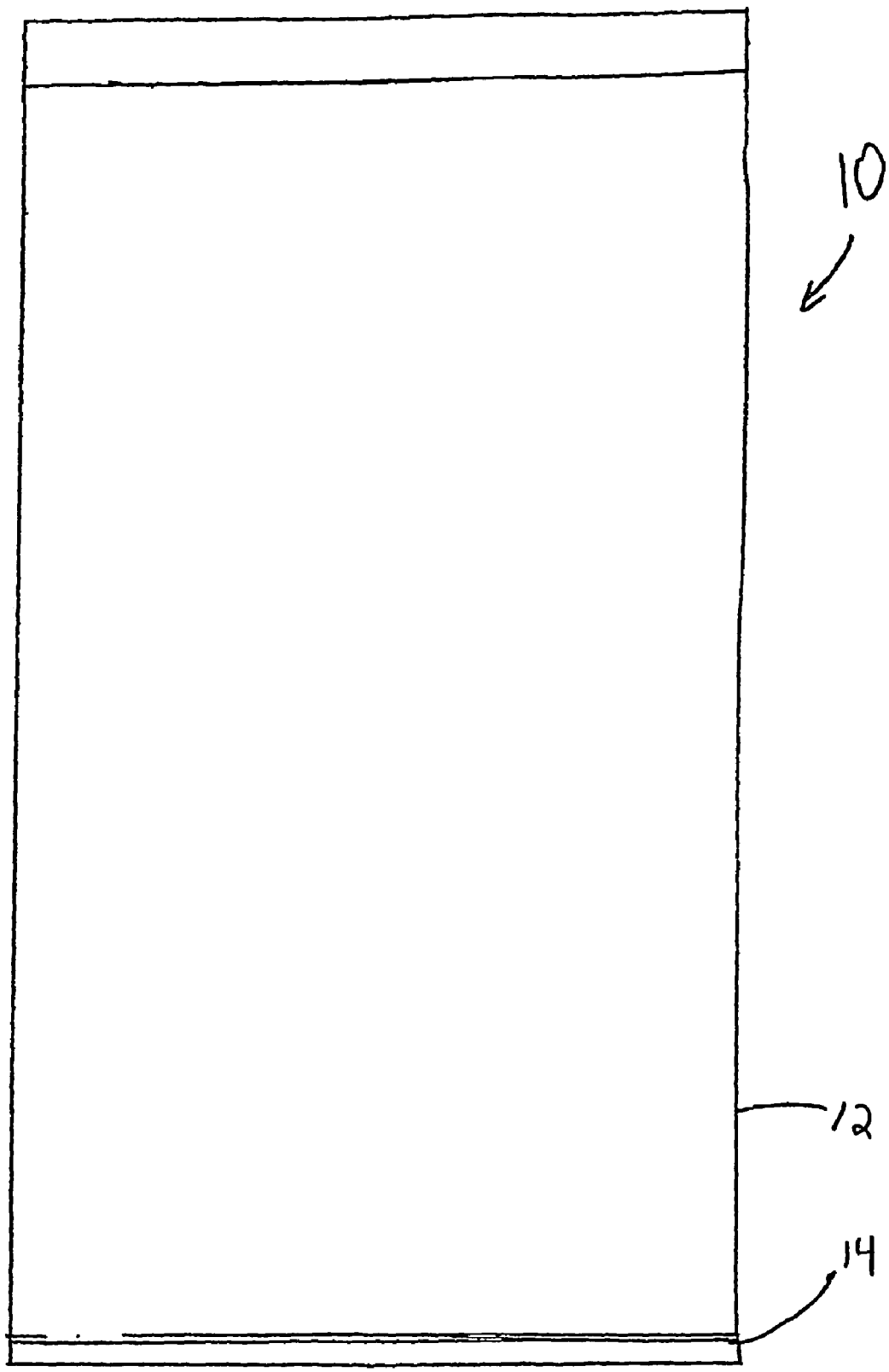
FIG. 1 is a top view of pressure measuring device, in accordance with one embodiment of the present invention.
Figure 2:
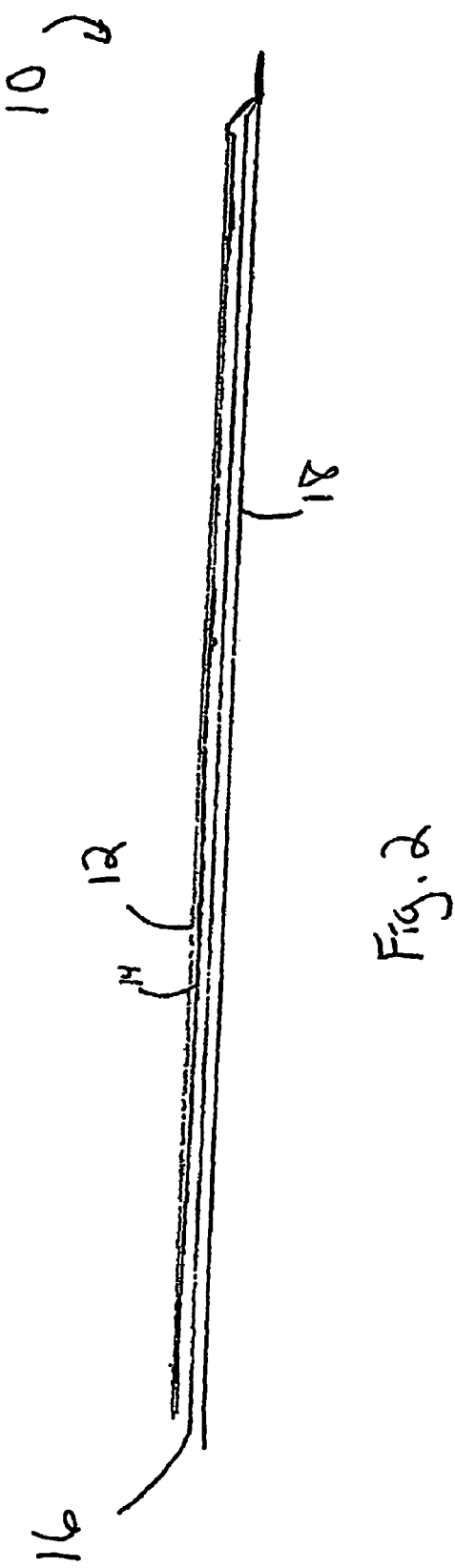
FIG. 2 is an exploded side view of the pressure measuring device of FIG. 1 showing the various layers, in accordance with one embodiment of the present invention.

In one embodiment of the present invention as illustrated in FIGS. 1 and 2, pressure measuring device is substantially rectangular in shape. Any similar shape may be used that is adequate to cover the entire underside of the patient's foot. A clear cover sheet 12 is provided that forms the top layer of the measuring device 10. The top surface of cover sheet 12 is smooth and is configured to provide a place for the patient to place their foot during testing.

Cover sheet 12 is provided with a sticky underside, configured to capture and adhere a certain portion of the pressure sensitive ink used during testing. A cover sheet backing layer 14 is provided such that the sticky underside of cover sheet 12 does not come into contact with the ink until the desired testing time. When pressure measuring device 10 is ready for use, cover layer 12 is lifted and backing layer 14 is removed. Cover layer 12 is then returned, sticky side down, to measuring device 10, placing device 10 into an active mode as discussed in more detail below.

Figure 3:
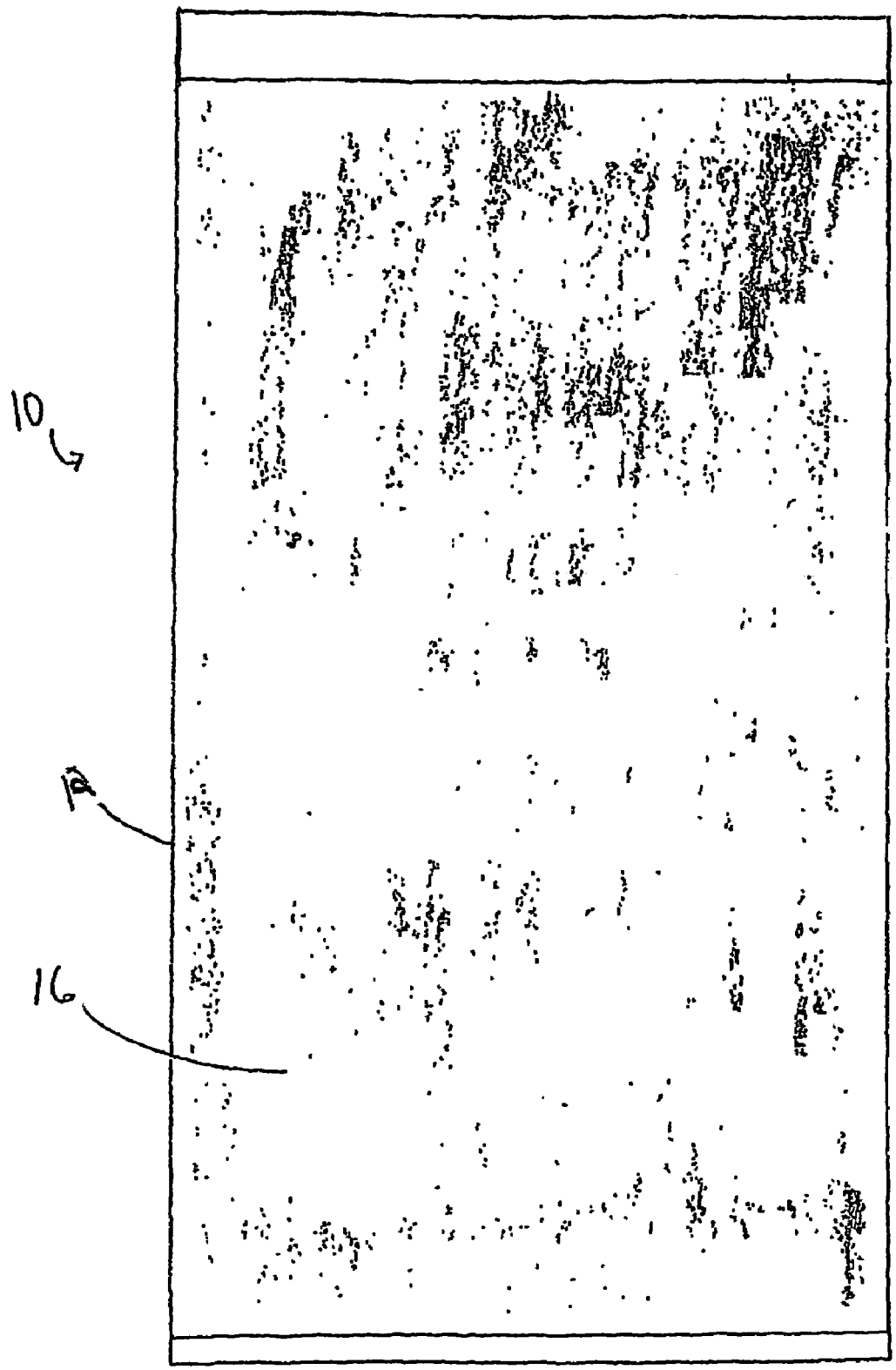
FIG. 3 is a top view of the pressure measuring device of FIG. 1 in an active mode, in accordance with one embodiment of the present invention.

As illustrated in FIGS. 2 and 3, below cover sheet 12 and backing layer 14, an ink/gelatin layer 16 is provided. Ink/gelatin layer 16 is coated with a pressure sensitive ink on its upper surface that is activated when the patient steps on the upper surface of cover layer 12. The pressure sensitive ink used on ink/gelatin layer 16 is configured to be transferred onto the sticky underside of cover sheet 12 and held in place forming a pressure foot print 20 relating to the plantar foot pressure of the patient's foot.

The pressure sensitive ink is preferably of a type that is sensitive between the ranges of 0 and 15 kg/cm$^2$ such that the pressure sensitive ink is placed onto the sticky underside when exposed to pressures within this range. The ink, in the form of pressure foot print 20, is deposited in the form of differentiable color density markings such as a gray-scale, where the areas under the least amount or no pressure are white and the areas under 9-15 kg/cm$^2$ or greater appear black, with various shades of gray for the in between pressures. It should be noted that various types of ink having different sensitivities may be used so long as they are capable of operating in the bounds typically found in measuring plantar foot pressure.

Figure 4:
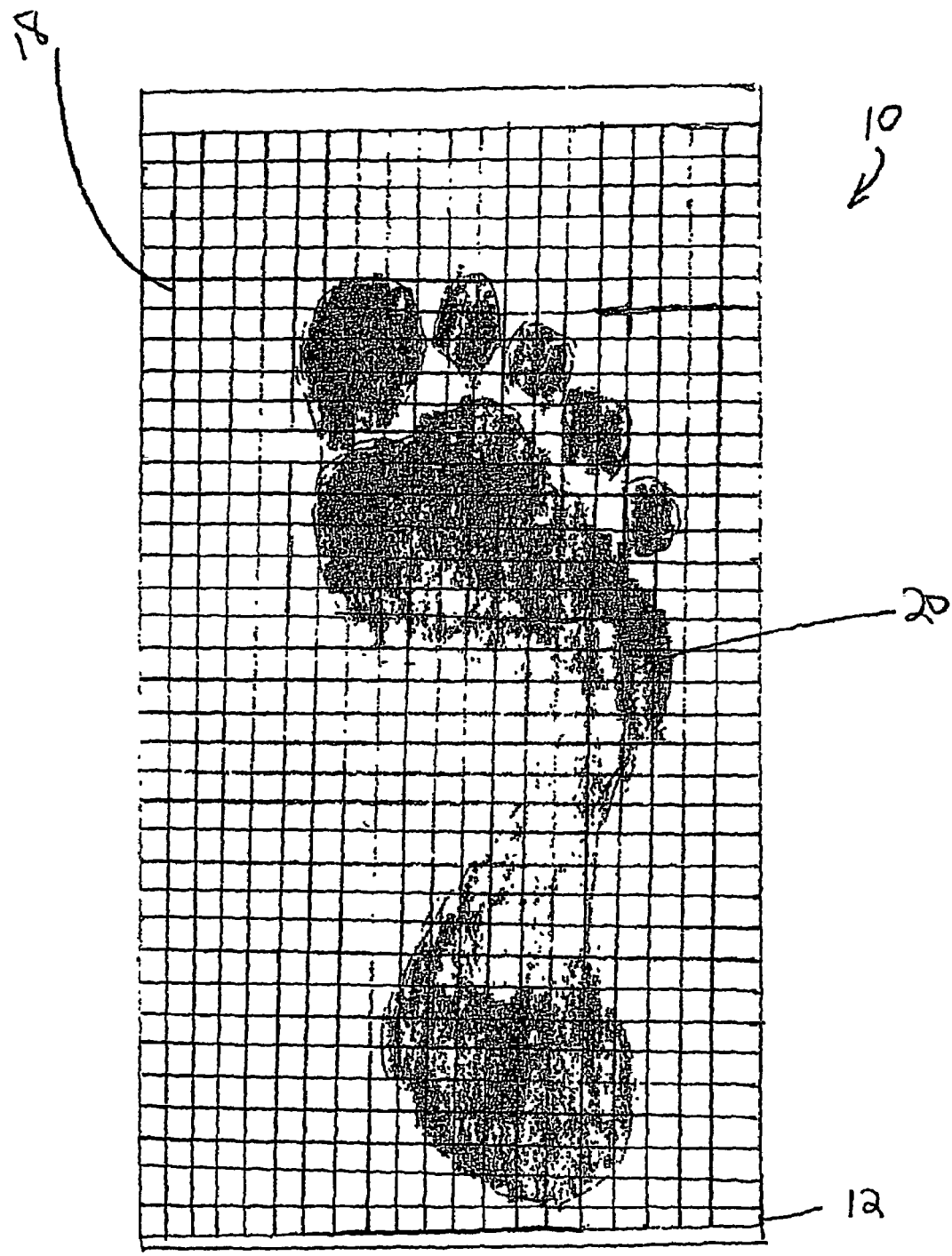
FIG. 4 is a top view of the pressure measuring device of FIG. 1 in a completed mode, in accordance with one embodiment of the present invention.
Figure 6:
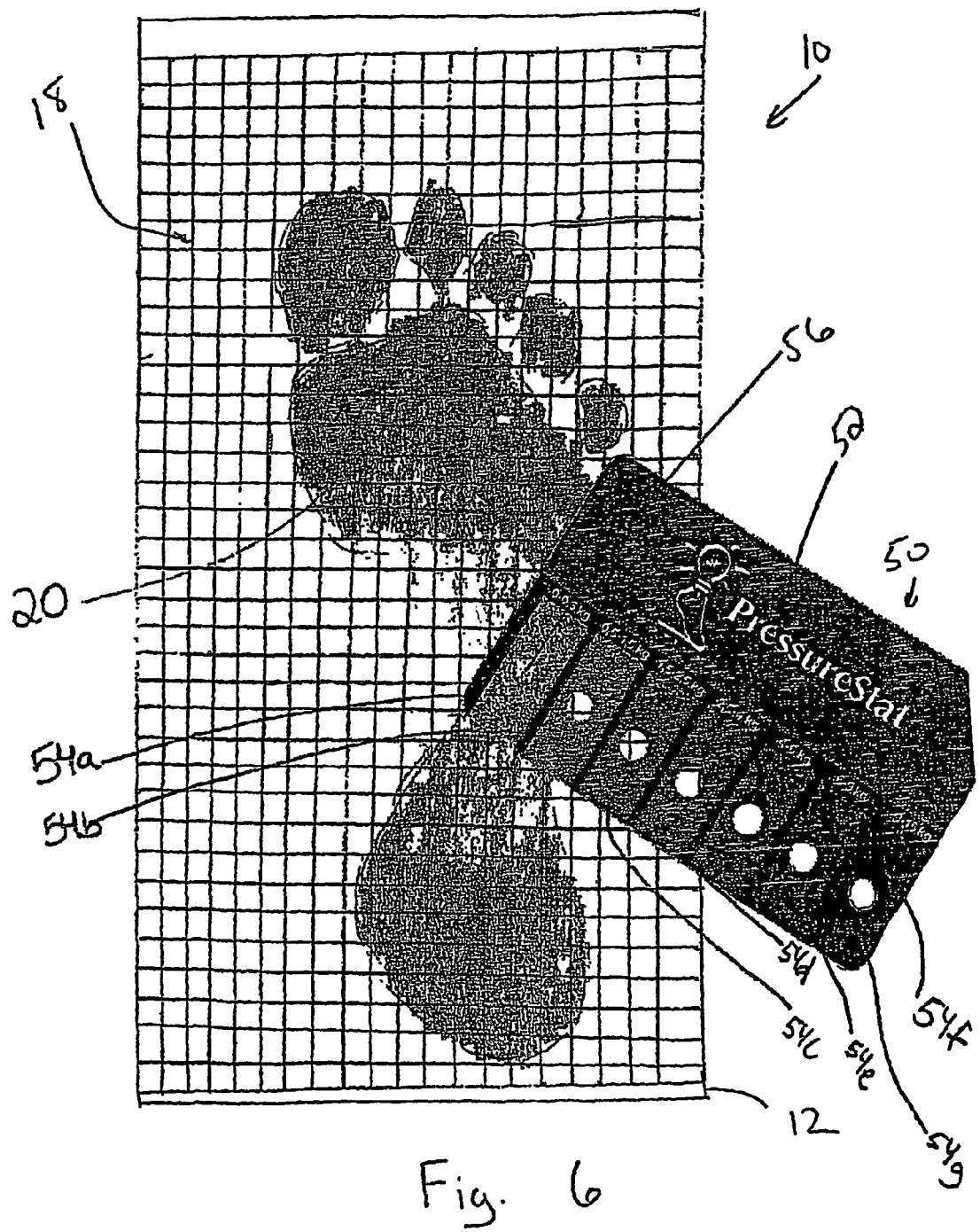
FIG. 6 illustrates the calibration card of FIG. 5 in use with the pressure measuring device in completed mode of FIG. 3, in accordance with one embodiment of the present invention.

In one embodiment of the present invention, as illustrated in FIGS. 2, 4 and 6, a grid sheet 18 is provided in measuring device 10. Grid sheet 18 forms the bottom layer of measuring device 10 and thus has the same shape as cover sheet 12 and is configured to provide a permanent sheet on which to affix the pressure sensitive ink from pressure foot print 20 that is held in the sticky underside of cover sheet 12. Grid sheet 18 is preferably brightly colored and highly contrasted to the ink used on ink/gelatin layer 16, however, this is no way intended to limit the scope of the present invention. Grid sheet 18 can be of any color or even transparent so long as the ink is both visible and measurable.

As illustrated in FIG. 4, when cover sheet 12 is placed on grid sheet 18 the pressure sensitive ink is fixed between cover sheet 12 and grid sheet 18, highlighting the gray-scale markings against grid-sheet 18. It should be noted that grid-sheet 18 is preferably white in color, however, any color grid sheet 18 which can be used as a proper back-drop for the gray-scale is within the contemplation of the present invention. Likewise, grid sheet 18 is preferably divided into a grid of 0.5 cm blocks, however, any size grid can be used as long as it is consistent with the pressure denomination used in the gray-scale. Markings or a ruler may be used along the edges of grid sheet 18 in order to provide further diagnostic markings.

Figure 5:
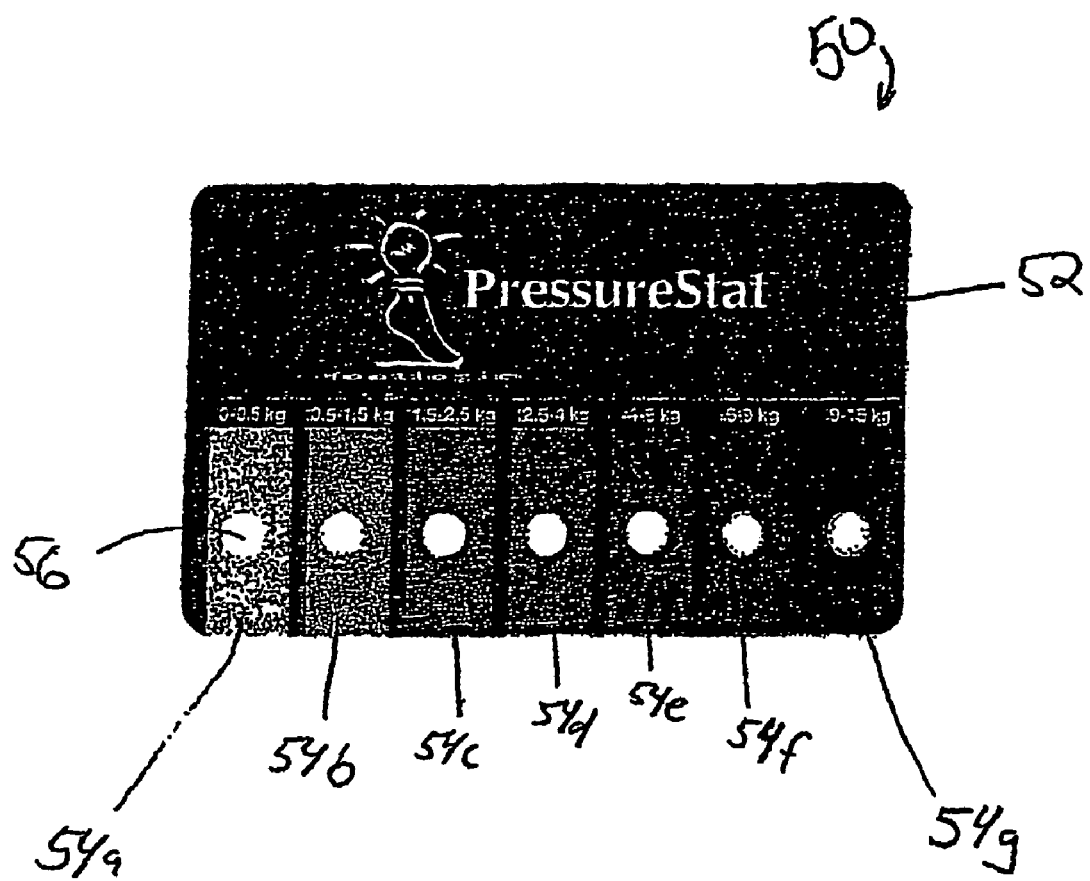
FIG. 5 is a top view of a calibration card in accordance with one embodiment of the present invention.

In one embodiment of the present invention as illustrated in FIG. 5 a calibration card 50 is provided, configured to provide the user with a means of reading the various gray ink markings from pressure foot print 20 on grid sheet 18. In this respect, the differentiable color density marking gray-scale, highlighted against grid sheet 18 is demarked in various shades of gray where lighter regions represent areas of low pressure and darker or black areas represent areas of higher pressure. Calibration card 50 is provided with corresponding differentiable color density markings such as gray-scale markings 52, that contain a series of pressure range regions 54a-54g, each having a gray-scale coloration density with an associated pressure range, where each coloration represents a different pressure range.

As illustrated in FIG. 5, pressure range region 54a corresponds to the color produced by a pressure of 0-0.5 kg/cm$^2$. Pressure range region 54b corresponds to the color produced by a pressure of 0.5-1.5 kg/cm$^2$. Pressure range region 54c corresponds to the color produced by a pressure of 1.5-2.5 kg/cm$^2$. Pressure range region 54d corresponds to the color produced by a pressure of 2.5-4 kg/cm$^2$. Pressure range region 54e corresponds to the color produced by a pressure of 4-6 kg/cm$^2$. Pressure range region 54f corresponds to the color produced by a pressure of 6-9 kg/cm$^2$. Pressure range region 54g corresponds to the color produced by a pressure of 9-15 kg/cm$^2$.

It should be noted that kg/cm$^2$ is used through out as illustrative of one method by which pressure can be measured, however this is in no way limited to the scope of the present invention. For example, lbs/in$^2$ or other pressure denominations can be used provided it is consistent between pressure measuring device 10 and calibration card 50.

As illustrated in FIG. 6, each pressure range region 54 on calibration card 50 is provided with a viewing opening 56 configured to allow the gray-scale pressure foot print 20 on grid sheet 18 to be viewed through calibration card 50 so that the plantar foot pressure for the area being calibrated can be determined.

Figure 7:
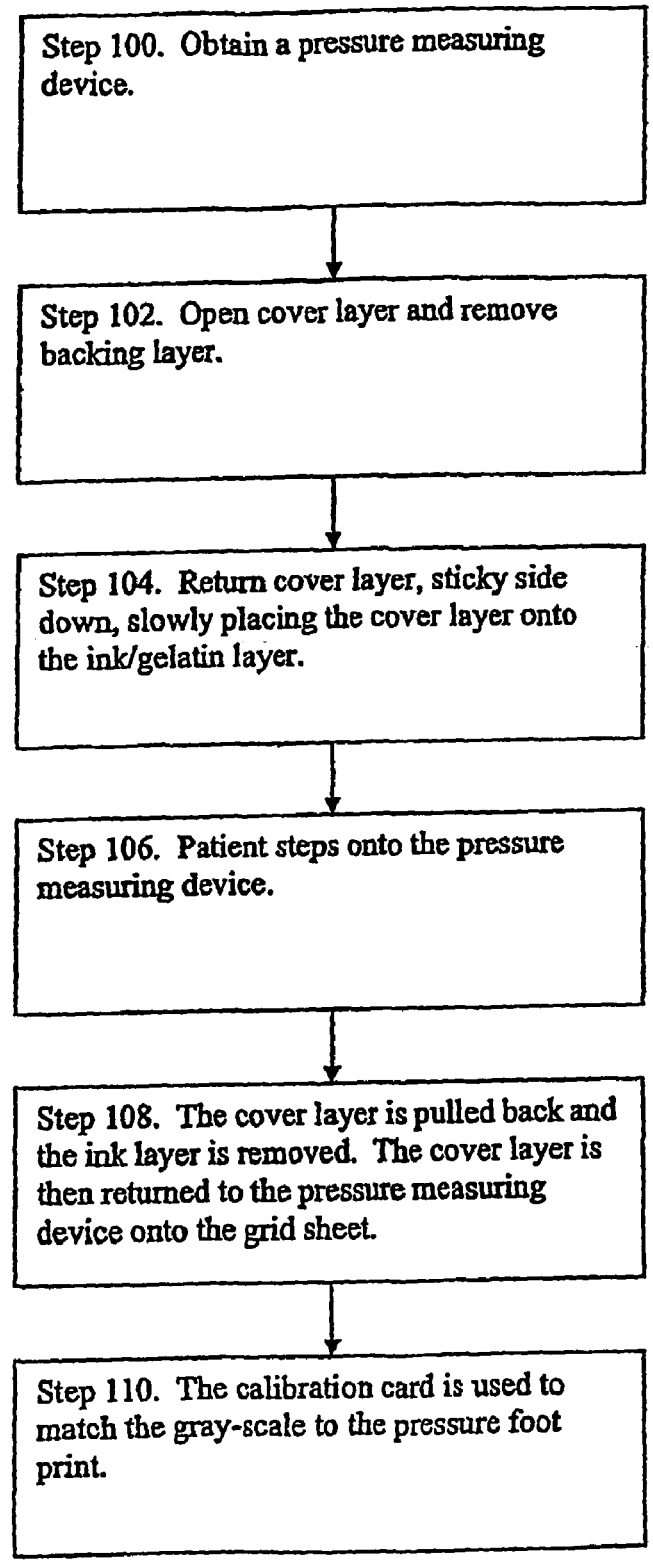
FIG. 7 is a flow chart detailing the operation of the pressure measuring device and calibration card, in accordance with one embodiment of the present invention.

In one embodiment of the present invention, as illustrated in flow chart FIG. 7, in operation, at step 100, the person administrating the planter foot pressure measurement obtains a pressure measuring device 10. Next, at step 102, cover layer 12 is pealed away from ink/gelatin layer 16 and backing layer 14 is removed exposing the sticky underside of cover layer 12.

At step 104, as illustrated in FIG. 3, cover layer 14 is then slowly placed back on top of ink/gelatin layer 16 so as to avoid any bubbles or wrinkles. This places pressure measuring device into an activated mode where the pressure sensitive ink is in direct contact with the stick underside of cover layer 12.

Next, at step 106, the patient is directed to step onto pressure measuring device 10, forming pressure foot print 20. This can be done in either a static or dynamic method. The static method requires that the patient step slowly onto measuring device 10 in a directly downward motion and then stand on device 10 so as to test the plantar foot pressure in a resting format. The dynamic method requires that the patient step onto measuring device 10 in a method consistent with the patient's normal walking gait so as to test the plantar foot pressure in a normal walking format.

It should be noted that other methods of obtaining the plantar pressure foot print 20 can also be used provided that the pressure resultant from the testing does not exceed or is not too low so as to be outside the range designated by the pressure sensitive ink being used.

Next, at step 108, the user again peals back cover sheet 12 with the ink form pressure foot print 20, attached to its sticky underside, and ink/gelatin layer 16 is removed. As illustrated in FIG. 4, cover sheet 12 is then placed slowly and carefully back down onto grid sheet 18 so as to avoid any bubbles or wrinkles, placing pressure measuring device 10 into a completed mode. In this configuration, the gray-scale plantar pressure foot print 20 is held permanently between cover sheet 12 and grid sheet 18 such that the pressure foot print 20 is readily viewable and readable against the bright background of grid sheet 18.

Next, as illustrated in FIG. 6, at step 110, the user obtains calibration card 50 and places it over the desired portion of the plantar pressure foot print 20. The gray-scale color of pressure foot print is then compared though viewing openings 56 with the various pressure range regions 54a-54g until a gray-scale density/color match is found. This step is repeated for all areas of interest on the plantar foot pressure print.

Thus, a cost effective and accurate means of determining plantar foot pressure is provided with a convenient calibration card for determining the results. As discussed above, when regions are found in the gray-scale print that exceeds 6 kg/cm$^2$, this may be an indication that further study of the affected area is warranted and the doctor may then take the appropriate steps.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A device for measuring plantar foot pressure, said device comprising:
   - a measuring device for generating an imprint of a patient's foot, said imprint including a first set of at least two differentiable color density markings, said first set of differentiable density markings each corresponding to a different pressure exerted on said measuring device by different areas of the patient's foot; and
   - a calibration card having an indicia thereon, said indicia including a second set of at least two differentiable color density markings, corresponding to said first set of differentiable density markings with like density markings referring to like pressure exerted on said measuring device, wherein each differentiable density marking in said second set of differentiable density markings on said calibration card has a viewing opening disposed within, such that when said viewing openings in said calibration card are placed over said imprint of said patients foot, the first set of differential density markings from said imprint are viewable through said viewing openings so that they are readily comparable to said second set of differentiable density markings in said indicia on said calibration card, allowing the pressure exerted by the patient's foot on a particular area of said imprint to be determined.

2. The device as claimed in claim 1, wherein said measuring device is a multi layered ink impression device.

3. The device as claimed in claim 1, wherein said measuring device is disposable.

4. The device as claimed in claim 1, wherein said first set of differentiable density markings on said imprint of the patient's footprint is a grayscale image.

5. The device as claimed in claim 4, wherein lighter regions in said grayscale depict areas of low pressure and wherein darker areas in said grayscale depict areas of higher pressure.

6. The device as claimed in claim 4, wherein said grayscale measures plantar foot pressure in the range of 0 kg/cm2 in white to 15 kg/cm$^2$ measured in black.

7. The device as claimed in claim 1, wherein said second set of differentiable density markings in said indicia on said calibration card is a grayscale.

8. The device as claimed in claim 7, wherein said each of said markings in said indicia grayscale correspond to a particular range of pressure.

9. The device as claimed in claim 8, wherein each of said markings in said indicia grayscale, corresponding to a particular range of pressures, each maintain its own viewing opening.

10. A method for measuring plantar foot pressure, said method comprising the steps of:
    - generating an imprint of a patient's foot using a measuring device, where said imprint includes a first set of at least two differentiable color density markings, said first set of differentiable density markings each corresponding to a different pressure exerted on said measuring device by different areas of the patient's foot;
    - placing a calibration card over said imprint of said patients foot, said calibration card having an indicia thereon including a second set of at least two differentiable color density markings, corresponding to said first set of differentiable density markings with like density markings referring to like pressure exerted on said measuring device, wherein each differentiable density marking in said second set of differentiable density markings on said calibration card has a viewing opening disposed within; and
    - determining the pressure exerted by the patient's foot on a particular area of said imprint using a calibration card, such that when said viewing openings in said calibration card are placed on said imprint, the first set of differential density markings from said imprint are viewable through said viewing openings so that they are readily comparable to said second set of differentiable density markings in said indicia on said calibration card for comparison.

* * * * *